(12) United States Patent
Rehner

(10) Patent No.: US 10,201,313 B2
(45) Date of Patent: Feb. 12, 2019

(54) MAGNETIC RESONANCE IMAGING SYSTEM FOR GENERATING A MAMMOGRAPHIC REPRESENTATION

(71) Applicant: Robert Rehner, Neunkirchen am Brand (DE)

(72) Inventor: Robert Rehner, Neunkirchen am Brand (DE)

(73) Assignee: Siemens Aktiengesellschaft, München (DE)

( * ) Notice: Subject to any disclaimer, the term of this patent is extended or adjusted under 35 U.S.C. 154(b) by 962 days.

(21) Appl. No.: 14/585,489

(22) Filed: Dec. 30, 2014

(65) Prior Publication Data

US 2015/0196255 A1    Jul. 16, 2015

(30) Foreign Application Priority Data

Jan. 10, 2014  (DE) ................ 10 2014 200 342

(51) Int. Cl.
  *A61B 5/055* (2006.01)
  *A61B 5/00* (2006.01)
  *G01R 33/387* (2006.01)

(52) U.S. Cl.
  CPC ............ *A61B 5/708* (2013.01); *A61B 5/0555* (2013.01); *A61B 5/4312* (2013.01); *G01R 33/387* (2013.01)

(58) Field of Classification Search
  None
  See application file for complete search history.

(56) References Cited

U.S. PATENT DOCUMENTS

| 4,680,549 A | 7/1987 | Tanttu |
| 5,699,802 A | 12/1997 | Duerr |
| 6,023,166 A | 2/2000 | Eydelman |

(Continued)

FOREIGN PATENT DOCUMENTS

| CN | 102792189 A | 11/2012 |
| CN | 103323798 A | 9/2013 |

(Continued)

OTHER PUBLICATIONS

German Office Action cited in DE102014200342.3, dated Aug. 29, 2014.

(Continued)

*Primary Examiner* — Jonathan Cwern
(74) *Attorney, Agent, or Firm* — Lempia Summerfield Katz LLC

(57) ABSTRACT

A magnetic resonance imaging system configured for generating a three-dimensional representation of at least one breast of a patient includes: a device configured for generating a homogeneous magnetic field; a system of active gradient coils configured for generating at least one magnetic field gradient within a measurement volume; at least one breast holder having an internal space configured for positioning the at least one breast during an MRI scan within the measurement volume; at least one local coil system that includes at least one individual coil, the at least one individual coil configured to act as an antenna for receiving magnetic resonance signals; and at least one cushion configured for stabilizing the at least one breast by filling the internal space between the at least one breast and an external boundary of the internal space.

20 Claims, 2 Drawing Sheets

(56) References Cited

U.S. PATENT DOCUMENTS

| | | | |
|---|---|---|---|
| 2003/0016017 A1* | 1/2003 | Reykowski | G01R 33/341 |
| | | | 324/322 |
| 2006/0270930 A1 | 11/2006 | Brasile | |
| 2008/0224708 A1* | 9/2008 | Mannerfelt | B60Q 1/305 |
| | | | 324/414 |
| 2009/0096456 A1 | 4/2009 | Biber et al. | |
| 2011/0152670 A1 | 6/2011 | Yang | |
| 2011/0241683 A1* | 10/2011 | Nnewihe | G01R 33/3415 |
| | | | 324/318 |
| 2011/0316539 A1 | 12/2011 | Lagendijk et al. | |
| 2013/0119988 A1* | 5/2013 | Driemel | G01R 33/34092 |
| | | | 324/322 |
| 2013/0249559 A1* | 9/2013 | Biber | A61B 5/055 |
| | | | 324/322 |

FOREIGN PATENT DOCUMENTS

| | | |
|---|---|---|
| DE | 4434949 | 4/1996 |
| DE | 102005024325 | 8/2006 |
| DE | 102007047020 | 7/2012 |
| DE | 102012204527 | 9/2013 |
| JP | S62182841 A | 8/1987 |
| JP | H0187711U U | 6/1989 |
| JP | H0515509A A | 1/1993 |
| JP | H0595943A A | 4/1993 |
| JP | 2013158429 A | 8/2013 |
| WO | WO2008114195 | 9/2008 |

OTHER PUBLICATIONS

Chinese Office Action for related Chinese Application No. 2014 105 735 09.5 dated Dec. 13, 2016, with English Translation.

Japanese Office Action for Japanese Application No. 2015-002287, dated Jul. 30, 2018.

* cited by examiner

MAGNETIC RESONANCE IMAGING SYSTEM FOR GENERATING A MAMMOGRAPHIC REPRESENTATION

RELATED APPLICATIONS

This application claims the benefit of German Patent Application No. DE 102014200342.3, filed Jan. 10, 2014. The entire contents of the priority document are hereby incorporated herein by reference.

TECHNICAL FIELD

The present teachings relate generally to a magnetic resonance imaging (MRI) system for generating a three-dimensional mammographic representation.

BACKGROUND

To diagnose disease in the breast tissue of women, dedicated local coil systems that may include a plurality of individual coils are used in magnetic resonance imaging to improve image quality (e.g., signal-to-noise ratio or SNR). For a magnetic resonance imaging examination of a breast, the patient is positioned in a prone position, such that one or both breasts may hang in cutouts in the local coil system. An optimized antenna array having a plurality of individual coils that act as MR reception antennas is placed around the openings in the interior of the housing of the local coil system. The individual coils are connected to the MRI system via active low-noise preamplifiers (LNAs).

To maximize the number of patients that may be examined using the local coil system, the cutouts in the local coil system may be configured to accommodate the maximum expected breast volume to be examined. However, the dimensions of the female breast vary greatly. As a result, although the local coil system has a high fill factor for patients with a large breast volume, the local coil system has a poor fill factor for patients with a small breast volume. Since the fill factor and, therefore, the distance of the tissue from the individual coils of the local coil system exert a direct influence on the achievable SNR, a loss in image quality may result for patients with a small breast volume.

The document DE 44 34 949 C2 describes an antenna arrangement of a local coil system for the magnetic resonance (MR) examination of a female breast. The problem of adaptation to different breast sizes is neither mentioned nor solved.

The document DE 10 2005 024 325 A1 describes a local coil system that is adapted for the MR examination of a female breast. The local coil system is in the form of a vest-shaped carrier part that the patient wears during examination. The vest-shaped carrier part may adapt itself to the female anatomy. With respect to the problem of adaptation to varying breast sizes, document DE 10 2005 024 325 A1 mentions only that breast tissue may be stabilized by insertion of a vacuum cushion. However, there is no description of adapting the antenna geometry to a smaller breast.

The document DE 10 2007 047 020 B4 describes an MRI system with an arrangement for transmitting magnetic resonance signals. The arrangement includes a local coil system for receiving radiofrequency signals from a magnetic resonance examination using a number of individual coils. The arrangement further includes passive individual antennae that are electromagnetically coupled to the individual coils of the local coil. The individual coils of the local coil system and the passive individual antennae are coupled to one another. Although the antenna arrangement described in document DE 10 2007 047 020 B4 presents a physical principle underlying improved SNR, the document does not describe any use of the principle within the field of mammographic MRI examinations. Moreover, the document does not describe the use of the principle with cushions for fixating the breast. Furthermore, the document does not describe any materials with a high permittivity.

SUMMARY AND DESCRIPTION

The scope of the present invention is defined solely by the appended claims, and is not affected to any degree by the statements within this summary.

The present embodiments may obviate one or more of the drawbacks or limitations in the related art. For example, in some embodiments, a MRI system for mammographic examinations is provided, wherein the SNR is maximized without modifying the size of the local coil system (e.g., even for different fill volumes of a local coil system due to different breast volumes of the patients to be examined).

In some embodiments, one or more of passive antenna structures that are resonant at the employed MR frequency (e.g., an antenna element or a whole antenna array made from a plurality of antenna elements) may be placed proximal to the breast tissue in the unfilled free space of the two breast coil cups and then inductively coupled to the active antenna elements that are further away. As a result, an SNR improvement is achieved since the passive self-oscillating antenna elements act in an amplifying manner with respect to the alternating magnetic field (e.g., B1 field) generated by the transmission coil. For breast imaging using MRI technology, cushions of different sizes may be used to stabilize differently sized breasts. In accordance with the present teachings, the cushions may be integrated with passive inductively coupling antenna elements. Thus, adaptation of the workflow for preparing the examination may be avoided. By way of example, the passive antenna elements may contain copper conductor tracks, or other materials with good electrical conductivity, disposed on a substrate material (e.g., an FR4 substrate material). Capacitors, inductors, an anti-parallel diode pair for passive detuning during the transmission, and a fuse may be placed on the substrate. Equipping the cushions with the passive antenna elements involves relatively low cost since active electronics and sheath wave chokes are unnecessary. Integrating the passive antenna elements into the stabilization cushions may allow the passive antenna elements to be reproducibly positioned in relation to the active individual coils of the local coil system, thereby facilitating reproducible optimization of the inductive coupling.

In place of the individual coils, the cushion used for breast stabilization may be manufactured from a material having a high relative permittivity (e.g., a value of at least 100). Such a material will have an amplifying effect with respect to the electromagnetic signals occurring in the measurement field. As a result, the active individual coils of the local coil system will be moved closer to the breast tissue in a virtual manner and, overall, lead to an improvement of the SNR of the electromagnetic signals to be measured. To maximize the SNR gain, the dielectric loss factor of the material may be minimized.

Filling the free space in the breast holder in accordance with the present teachings does not hinder the present workflow of a medical assistant and, therefore, does not result in an increased workload.

A magnetic resonance imaging (MRI) system in accordance with the present teachings for generating three-dimensional representations of at least one breast of a patient includes: a device configured for generating a homogeneous magnetic field; a system of active gradient coils configured for generating at least one magnetic field gradient within a measurement volume; at least one breast holder having an internal space configured for positioning the breast during an MRI scan within the measurement volume; at least one local coil system made of at least one individual coil acting as an antenna for receiving magnetic resonance signals; and at least one cushion configured for stabilizing the breast by filling the internal space between the breast and an external boundary of the internal space. The at least one breast holder includes at least one cushion in the internal space. The cushion is configured to generate electromagnetic coupling in the region of the magnetic resonance to the at least one individual coil of the local coil system.

In an MRI system configured for mammography in accordance with the present teachings, inserts may be provided for fixating breasts of various sizes, such that a reproducible shaping of the breast with ideal positioning of the antenna elements in relation to the breast tissue may be achieved independently of the patient's anatomy. Moreover, as a result of the reproducible shaping of the breast, comparability of examination results obtained multiple times over relatively long time intervals may be achieved, and localization of lesions in real breast tissue may be facilitated. If a radiologist does not want the breasts to be stabilized, the cushions may be used with small breasts for increasing the SNR with a slightly increased workflow complexity.

In some embodiments, an MRI system in accordance with the present teachings may be configured such that the at least one cushion includes at least one passive antenna element that is configured for inductive coupling with the at least one individual coil of the local coil system. The at least one passive antenna element may be configured, for example, as a copper conductor track on a substrate (e.g., an FR4 substrate).

In some embodiments, the at least one antenna element includes at least one capacitor and at least one inductor. In some embodiments, the at least one antenna element may include an anti-parallel diode pair configured for passive detuning during transmission and/or a fuse. The combination of conductor tracks and capacitors may be selected such that the antenna structure resonates at the MR frequency, therefore causing maximum field amplification. In one embodiment, a value of the at least one inductor is selected such that the at least one inductor and the at least one capacitor are resonant at a magnetic resonance frequency used in the MRI system, and such that the at least one passive antenna element is detuned for transmission. The value of the at least one inductor may also be selected such that the at least one passive antenna element is detuned for transmission.

In alternative embodiments, self-resonant antennas without additional concentrated capacitors may be used. For example, passive antennae for coupling the signals to be measured (as described, for example, in document DE 10 2007 047 020 B4) may be used.

In some embodiments, the coupling of the local coil to a resonator situated close to the breast tissue may be implemented by having the at least one cushion contain a material with high relative permittivity. For example, the relative permittivity may have a value of at least 100. By using such a material to pad the free volume between breast tissue and local coil, a microscopic antenna structure for coupling the measurement signals may be provided at the molecular level in place of the macroscopic antenna structure.

To achieve reproducible and uniquely defined coupling and shaping, the breast holder and the at least one cushion may include complementary positioning structures that permit a unique positioning of the cushions in the breast holder. Moreover, the breast holder may include a plurality of interchangeable cushion sets for different breast sizes.

In some embodiments, the active local coil system includes a plurality of individual coils.

In some embodiments, a breast holder with one local coil system may be provided for each breast to be examined. Thus, both female breasts may be simultaneously examined during a single examination. However, in other embodiments, a single breast holder with a single local coil may be used instead (e.g., with a patient having previously undergone a breast amputation as a result of earlier positive findings). In some embodiments, to accommodate a patient having differently sized breasts, two cushions with different dimensions may be present in the two openings of the breast holder with correspondingly differently disposed passive antenna elements.

In some embodiments, a patient couch configured for horizontal support of the patient may be provided. The patient couch may include one opening, respectively, for each breast to be examined. A breast holder with one local coil may be assigned to each opening.

With minimal technical outlay and at low cost, an MRI system in accordance with the present teachings may be used to improve the SNR for patients with small breast volumes. Complicated mechanical structures that are at risk of wear and tear may not be needed to implement displaceable active antenna elements. The integration of passive antenna structures or material with high relative permittivity into breast stabilization cushions does not cause a change in the workflow of the radiography assistant. Conventional cushions may be readily replaced by cushions in accordance with the present teachings, such that conventional breast holders with local coils may be equipped with cushions in accordance with the present teachings.

BRIEF DESCRIPTION OF THE DRAWINGS

In the drawings, only features relevant to an understanding of the accompanying detailed description are displayed.

DETAILED DESCRIPTION

Figure 1:
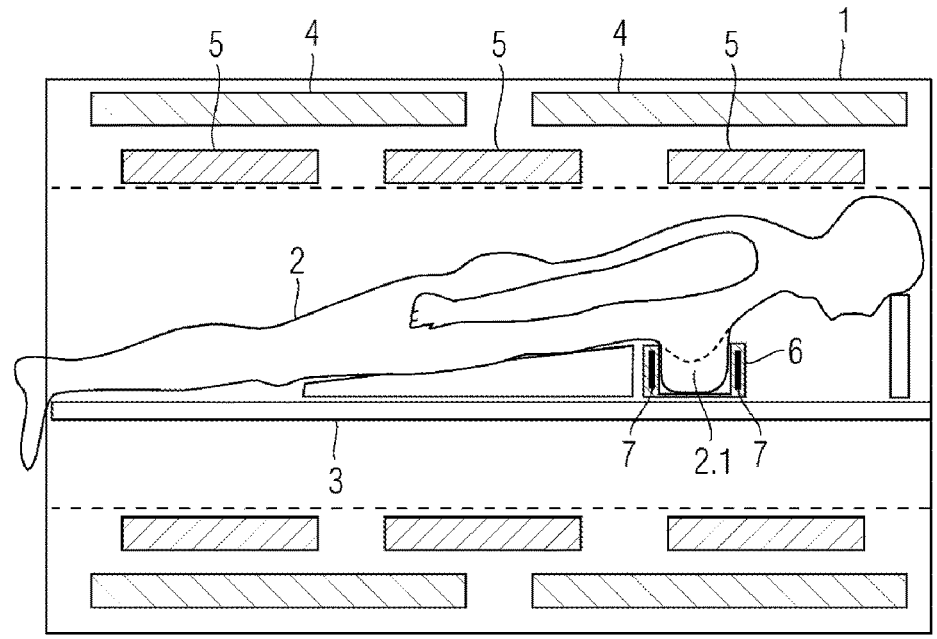
FIG. 1 shows an example of an MRI system with a conventional breast holder.

FIG. 1 shows a schematic cross-sectional view of an MRI system 1 wherein a patient 2 is supported on a patient couch 3 in the measurement region. The measurement region is defined by a first set of magnetic coils 4. The magnetic coils 4 establish a homogeneous magnetic field during the MR examination. A second set of magnetic coils 5 is installed for generating the gradient field. To assist the measurement, local coils that may be placed at locations of interest may be used in the measurement region in a conventional manner. For a mammographic MR examination, a breast holder 6 may be used that contains the local coil system. The local coil system contains a plurality of individual coils 7 and may be used to record the measurement signals from the region of the breast. Since the exemplary patient 2 shown in FIG. 1 has a relatively large breast 2.1 that substantially fills the breast holder 6 with the local coil system, the individual coils are already situated close to the breast tissue and an additional coupling element to improve the transmission of the measurement signals is not needed. The dashed line on the large breast 2.1 represents an example of a small breast that does not fill the breast holder 6. With the smaller breast indicated by the dashed line, there is a relatively large distance between the individual coils 7 of the local coil system and the breast tissue during examination. As a result, there is a deterioration in the SNR.

Figure 2:
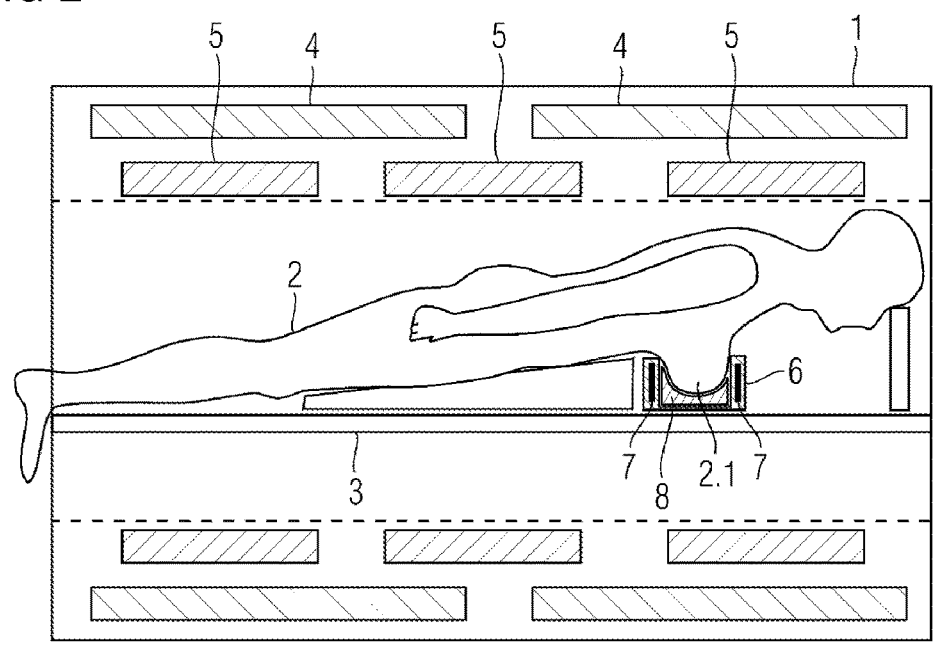
FIG. 2 shows an example of an MRI system with a breast holder and a local coil system for the breast that includes an inserted cushion made of a material with a high relative permittivity for coupling the measurement signals.

FIG. 2 shows a schematic illustration of an MRI system 1 being used for the examination of a different patient 2 having a slightly smaller breast 2.1. As a result of the smaller breast 2.1, the distance between the breast tissue and the individual coils 7 of the local coil system substantially increases. Thus, without additional measures, a deterioration in the SNR of the received measurement signal may be expected. In accordance with the present teachings, a cushion 8 that contains material with a high permittivity (e.g., with a high relative permittivity) may be used for positioning the breast in the breast holder 6 with the local coil system integrated therein. As a result, the measurement signals emitted by the breast tissue are forwarded in an improved manner to the individual coils 7 of the local coil system. As a result, an improvement in the SNR of the measurement signals may be achieved relative to a measurement without the cushion 8.

Figure 3:
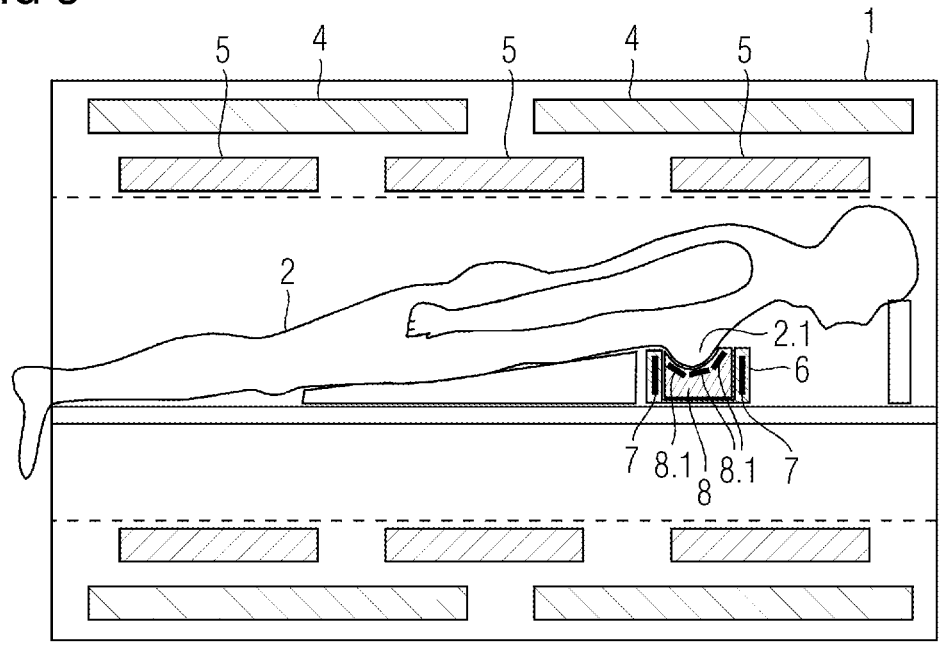
FIG. 3 shows an example of an MRI system with a breast holder and a local coil system for the breast that includes an inserted cushion with additional passive coils for coupling the measurement signals.

FIG. 3 shows another schematic illustration of the same MRI system 1 shown in FIGS. 1 and 2. As in FIG. 2, the patient 2 shown in FIG. 3 has a relatively small breast 2.1. Due to the relatively small breast 2.1, the distance between the breast tissue and the individual coils 7 of the local coil system once again substantially increases. As a result, without additional measures, a deterioration in the SNR of the received measurement signal may be expected.

In accordance with the present teachings, a cushion 8 that, as shown in FIG. 3, may include passive antenna elements 8.1 is inserted into the breast holder 6 containing the individual coils 7 of the local coil system. The passive antenna elements 8.1 are configured to generate electromagnetic coupling to the active individual coils 7, thereby resulting in improved SNR of the transmitted measurement signals due to the spatial proximity to the breast 2.1. The cushions 8 fill the otherwise empty space between the breast holder 6 and the breast tissue. As a result, the breast tissue may be stabilized and positioned as desired.

In FIGS. 1-3, examples of additional support aids (e.g., a wedge, a headrest) are shown but without corresponding reference characters. These support aids are optional and non-essential.

Figure 4:
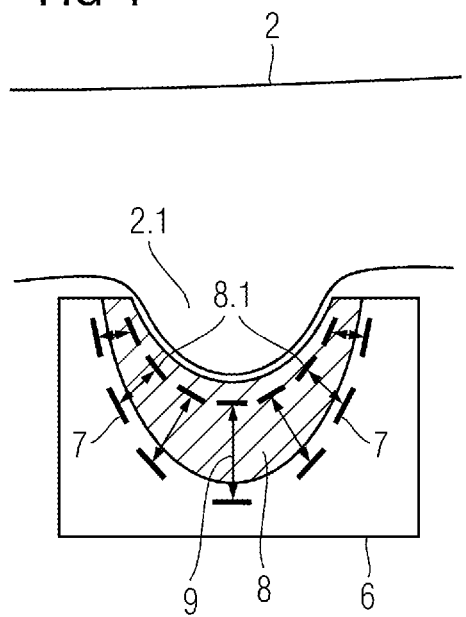
FIG. 4 shows an example of a breast holder with an integrated local coil system that includes an inserted cushion with passively amplifying antenna structures.

FIG. 4 shows a detailed view of an alternative breast holder 6 having an integrated local coil that contains a plurality of individual coils 7 and a breast 2.1. The breast 2.1 disposed in the breast holder 6 as shown in FIG. 4 is relatively small compared to the breast holder 6. In accordance with the present teachings, a cushion 8 with a plurality of integrated passive antenna elements 8.1 is situated in the interspace between the inner wall of the breast holder 6 and the breast tissue of the breast 2.1. The passive antenna elements 8.1 are configured to generate electromagnetic coupling to the active individual coils 7, thereby resulting in an improved SNR of the transmitted measurement signals due to the spatial proximity to the breast 2.1. The inductive coupling between the individual coils 7 and the passive antenna elements 8.1 is described by the arrows 9. In the example shown in FIG. 4, a passive antenna element may be assigned to each active antenna element to optimize the power of the resulting overall system.

Figure 5:
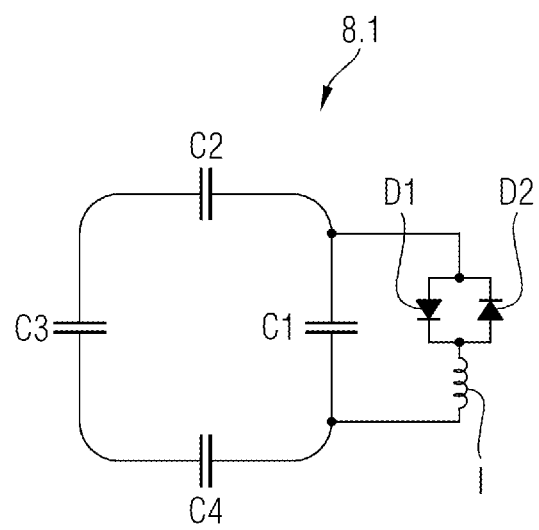
FIG. 5 shows an example of a circuit arrangement of a passively amplifying antenna structure.

An exemplary circuit diagram of an antenna element 8.1 with passive detuning is shown in FIG. 5. The antenna element 8.1 contains four capacitors C1 to C4 connected in a ring-shaped manner. For passive detuning, the two sides of one capacitor C1 are connected in series via an inductor I with two oppositely directed diodes D1 and D2 connected in parallel.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The invention claimed is:

1. A magnetic resonance imaging (MRI) system configured for generating a three-dimensional representation of at least one breast of a patient, the MRI system comprising:
   magnetic coils configured for generating a homogeneous magnetic field;
   a system of active gradient coils configured for generating at least one magnetic field gradient within a measurement volume;
   at least one breast holder comprising an internal space configured for positioning the at least one breast during an MRI scan within the measurement volume;
   at least one local coil system comprising at least one individual coil, the at least one individual coil configured to act as an antenna for receiving magnetic resonance signals; and
   at least one cushion configured for stabilizing the at least one breast by filling the internal space between the at least one breast and an external boundary of the internal space;
      wherein the at least one breast holder comprises the at least one cushion in the internal space, wherein the at least one cushion is configured to generate electromagnetic coupling in a region of magnetic resonance to the at least one individual coil of the at least one local coil system,
      wherein the at least one cushion comprises at least one passive antenna element, wherein the at least one passive antenna element is configured for inductive coupling with the at least one individual coil, wherein the at least one passive antenna element is adapted to be positioned adjacent to a surface of the at least one breast of the patient such that the at least one passive antenna element is disposed within the at least one cushion between an inner wall of the at least one breast holder and a surface of the at least one breast of the patient, and wherein the at least one individual coil is disposed within the at least one breast holder at a distance from the at least one passive antenna element such that the at least one individual coil is positioned outside the at least one cushion.

2. The MRI system of claim 1, wherein the at least one passive antenna element is configured as a conductor track on a substrate.

3. The MRI system of claim 2 wherein the conductor track comprises copper.

4. The MRI system of claim 2, wherein the at least one passive antenna element comprises an element selected from the group consisting of at least one capacitor and at least one inductor, an anti-parallel diode pair configured for passive detuning during transmission, a fuse, and combinations thereof.

5. The MRI system claim 4, wherein a capacitance of the at least one capacitor is selected such that the at least one passive antenna element is resonant at a magnetic resonance frequency.

6. The MRI system of claim 5, wherein a value of the at least one inductor is selected such that the at least one inductor is resonant at a magnetic resonance frequency used in the MRI system, and wherein the at least one passive antenna element comprises the anti-parallel diode pair, such that the at least one passive antenna element is detuned for transmission.

7. The MRI system of claim 4, wherein a value of the at least one inductor is selected such that the at least one inductor is resonant at a magnetic resonance frequency used in the MRI system, and wherein the at least one passive antenna element comprises the anti-parallel diode pair, such that at least one passive antenna element is detuned for transmission.

8. The MRI system of claim 2, wherein the at least one breast holder comprises a first positioning structure, and wherein the at least one cushion comprises a complementary second positioning structure, wherein the first positioning structure and the complementary second positioning structure together provide a positioning of the at least one cushion in the at least one breast holder.

9. The MRI system of claim 1, wherein the at least one passive antenna element comprises an element selected from the group consisting of at least one capacitor and at least one inductor, an anti-parallel diode pair configured for passive detuning during transmission, a fuse, and combinations thereof.

10. The MRI system claim 9, wherein a capacitance of the at least one capacitor is selected such that the at least one passive antenna element is resonant at a magnetic resonance frequency.

11. The MRI system of claim 10, wherein a value of the at least one inductor is selected such that the at least one inductor is resonant at a magnetic resonance frequency used in the MRI system, and wherein the at least one passive antenna element comprises the anti-parallel diode pair,such that the at least one passive antenna element is detuned for transmission.

12. The MRI system of claim 9, wherein a value of the at least one inductor is selected such that the at least one inductor is resonant at a magnetic resonance frequency used in the MRI system, and wherein the at least one passive antenna element comprises the anti-parallel diode pair, such that the at least one passive antenna element is detuned for transmission.

13. The MRI system of claim 1, wherein the at least one cushion comprises a material having a high relative permittivity.

14. The MRI system of claim 13, wherein the relative permittivity has a value of at least 100.

15. The MRI system of claim 1, wherein the at least one breast holder comprises a first positioning structure, and wherein the at least one cushion comprises a complementary second positioning structure, wherein the first positioning structure and the complementary second positioning structure together provide a positioning of the at least one cushion in the at least one breast holder.

16. The MRI system of claim 1, wherein the at least one cushion is interchangeable with a plurality of interchangeable cushion sets, wherein each cushion of the plurality of interchangeable cushion sets is configured for different breast sizes.

17. The MRI system of claim 1, wherein the at least one local coil system comprises a plurality of individual coils.

18. The MRI system of claim 1, further comprising a patient couch configured for horizontal support of the patient, wherein the patient couch comprises a respective opening for each breast to be examined, wherein the at least one breast holder comprises two breast holders assigned to each respective opening, and wherein each of the two breast holders comprise a local coil system. complementary second positioning structure together provide a positioning of the at least one cushion in the at least one breast holder.

19. A magnetic resonance imaging (MRI) system configured for generating a three-dimensional representation of at least one breast of a patient, the MRI system comprising:
　a system of magnetic coils configured for generating a homogeneous magnetic field;
　a system of active gradient coils configured for generating at least one magnetic field gradient within a measurement volume;
　at least one breast holder comprising an internal space configured for positioning the at least one breast during an MRI scan within the measurement volume;
　at least one local coil system comprising at least one individual coil, the at least one individual coil configured to act as an antenna for receiving magnetic resonance signals; and
　at least one cushion configured for stabilizing the at least one breast by filling the internal space between the at least one breast and an external boundary of the internal space, the at least one cushion comprising at least one passive antenna element;
　　wherein the at least one breast holder comprises the at least one cushion in the internal space, wherein the at least one cushion is configured to generate electromagnetic coupling in a region of magnetic resonance of the at least one passive antenna element to the at least one individual coil of the at least one local coil system,
　　wherein the at least on passive antenna element is disposed within the at least one cushion and adapted to be positioned adjacent to a surface of the at least one breast of the patient,
　　wherein the at least one individual coil is disposed outside of the at least one cushion, and wherein the at least one cushion comprises a material having a relative permittivity value of at least 100.

20. The MRI system of claim 19, wherein the at least one breast holder comprises a first positioning structure, and wherein the at least one cushion comprises a complementary second positioning structure, wherein the first positioning structure and the complementary second positioning structure together provide a positioning of the at least one cushion in the at least one breast holder.

\* \* \* \* \*

UNITED STATES PATENT AND TRADEMARK OFFICE
CERTIFICATE OF CORRECTION

PATENT NO. : 10,201,313 B2
APPLICATION NO. : 14/585489
DATED : February 12, 2019
INVENTOR(S) : Robert Rehner It is certified that error appears in the above-identified patent and that said Letters Patent is hereby corrected as shown below:

In the Claims

Column 8, In Claim 18 (Lines 32 – 34): "complementary second positioning structure together provide a positioning of the at least one cushion in the at least one breast holder." –should be removed–

Signed and Sealed this
Eighteenth Day of June, 2019

Andrei Iancu
*Director of the United States Patent and Trademark Office*